(12) United States Patent
Park et al.

(10) Patent No.: US 8,828,334 B2
(45) Date of Patent: Sep. 9, 2014

(54) MODULE FOR DETECTING ANALYTES IN FLUIDS AND CHIP HAVING THE SAME

(75) Inventors: Jun Ha Park, Suwon-si (KR); Chang Seop Lee, Ansan-si (KR); Hyun Chang Lim, Seoul (KR); Chan Il Chung, Seoul (KR); Jun Keun Chang, Seoul (KR)

(73) Assignee: Nanoentek, Inc., Seoul (KR)

( * ) Notice: Subject to any disclaimer, the term of this patent is extended or adjusted under 35 U.S.C. 154(b) by 1176 days.

(21) Appl. No.: 12/667,374

(22) PCT Filed: Jul. 23, 2008

(86) PCT No.: PCT/KR2008/004315
§ 371 (c)(1),
(2), (4) Date: Jul. 13, 2011

(87) PCT Pub. No.: WO2009/014380
PCT Pub. Date: Jan. 29, 2009

(65) Prior Publication Data
US 2011/0294197 A1  Dec. 1, 2011

(30) Foreign Application Priority Data
Jul. 23, 2007  (KR) .................. 10-2007-0073657

(51) Int. Cl.
*B01L 99/00* (2010.01)
*B01L 3/00* (2006.01)

(52) U.S. Cl.
CPC ......... *B01L 3/502753* (2013.01); *B01L 3/5027* (2013.01); *B01L 2300/0681* (2013.01); *B01L 2300/0825* (2013.01); *B01L 2400/0406* (2013.01)
USPC .......................................... 422/503; 422/507

(58) Field of Classification Search
CPC ................................. B81B 1/00; B01L 3/5027
USPC ..................................................... 422/502–507
See application file for complete search history.

(56) References Cited

U.S. PATENT DOCUMENTS

| 4,790,640 | A | | 12/1988 | Nason |
| 5,135,719 | A | | 8/1992 | Hillman et al. |
| 5,147,606 | A | | 9/1992 | Charlton et al. |
| 5,726,026 | A | * | 3/1998 | Wilding et al. ............ 435/7.21 |

FOREIGN PATENT DOCUMENTS

| CN | 1930480 | 3/2007 |
| JP | 06-010900 | 1/1994 |
| JP | 2005512071 | 6/2003 |
| KR | 1020060017701 | 2/2006 |
| WO | 03/037514 | 5/2003 |
| WO | WO 2005/119211 A1 * | 12/2005 |

OTHER PUBLICATIONS

Office Action for Japanese Application No. 2010-514651.

(Continued)

*Primary Examiner* — Paul Hyun
(74) *Attorney, Agent, or Firm* — Sherr & Jiang, PLLC

(57) ABSTRACT

Disclosed is a module for rapidly detecting analytes in fluids with high effectiveness and a chip having the module. The module includes a microchannel, which has a filtering zone for removing noise materials and a reaction zone wherein labeling reaction and immobilization reaction for detection of analytes are performed, sample fluid moving through the microchannel due to capillary floating. In a case where the chip having the module is used in detecting analytes in fluids, it is possible to minimize dead volume of sample fluid so that high effective volume ratio can be implemented. Therefore, the chip can be used in detecting analytes from the minimum amount of sample fluid.

11 Claims, 14 Drawing Sheets

(56) References Cited

OTHER PUBLICATIONS

Office Action for Chinese Application 200880022891.3 (Jul. 30, 2012).

International Search Report from Application PCT/KR2008/004315, date mailed Feb. 5, 2009.

* cited by examiner

MODULE FOR DETECTING ANALYTES IN FLUIDS AND CHIP HAVING THE SAME

CROSS-REFERENCES TO RELATED APPLICATIONS

This application is a U.S. national phase application, pursuant to 35 U.S.C. §371 of PCT/KR2008/004315, filed Jul. 23, 2008, designating the United States, which claims priority to Korean Application No. 10-2007-0073657, filed Jul. 23, 2007. The entire contents of the aforementioned patent applications are incorporated herein by this reference.

TECHNICAL FIELD

The present invention relates to a module for detecting analytes in fluids and a chip having the same, and more particularly to a module for rapidly detecting analytes in fluids moving through a microchannel due to capillary floating in high efficiency, and a chip having the module.

BACKGROUND ART

A lab-on-a-chip is a chip where various test processes are performed in a laboratory, for example, separation, refinement, mixing, labeling, analysis, and washing, etc. of a sample, on a chip having a small size. Techniques related to microfluidics and a micro-LHS are typically used in designing the lab-on-a-chip. Also, in manufacturing a chip-structure implementing microfluidics and the micro-LHS, a chip, in which a microchannel is formed at the interior of the chip by using a semiconductor circuit designing technique, has been put on the market. For example, in a microarray chip, material to be detected and a probe to be reacted, e.g. protein or DNA, are adhered on a substrate with a predetermined interval, and material to be coupled with them is detected. Therefore, the microarray chip is used in diagnosing trouble or disease. A chip where proteins are arranged is a microarray protein-chip, and a chip where DNA is arranged is a micro DNA chip. Analytes existing in blood, for example, proteins, antibodies, etc. exist in a very small amount. Therefore, an attempt to increase detecting efficiency by increasing the degree of integration of probes arrayed on a substrate has been continuously performed. As a result, a nanoarray chip, which increases integration of probes to a nano-level, has been reported.

In general, analysis of a sample fluid is typically used in analyzing blood and body fluid collected from a patient and in diagnosing disease through the analysis, as well as in a chemistry and bio-technical field. As such, detecting and analyzing analytes in a very small amount, which are included in sample fluid, such as blood, a body fluid, urine, etc., includes analyzing if a sample fluid reacts against proteins, such as antigens, antibodies, etc., DNA/RNA, a receptor, or other material, which have previously immobilized on a chip, while moving through a channel having a pipe-shaped structure formed in the interior of the chip, through a detecting signal using an optical means, such as a fluorescent material, etc. or an electric means. In analyzing a sample fluid, it is very important in a biochip, as well as a lab-on-a-chip, to analyze a sample in a very minimum amount.

In general, a lab-on-a-chip for analyzing a sample fluid includes: a sample injecting part for supplying sample fluid to the chip; a filtering zone using a paper filter so as to remove noise material, except for analytes in fluids; a reaction zone where binding between anlaytes and detection signal generating material, e.g. fluorescent material is performed, and reaction between the analytes bonded to the detection signal generating material and material, which is immobilized on a substrate to specially react against the analytes, is performed; and a detection zone for detecting anlaytes, such as blood, urine, proteins in body fluids, etc., by using a chip, and detecting detection signals through a connected detection apparatus.

Whole blood includes plasma (46~63%) and blood corpuscles (37~54%) having red blood cells (donut-shape, diameter: 7~8 μm/thickness: 2 μm, 50% of blood), leukocytes (a non-regular spherical shape, diameter: 10~20 μm), and platelets (diameter: 1~3 μm). In addition to plasma and blood corpuscle, various kinds of analytes, which can be used in diagnosing troubles and diseases, e.g. protein, antigens and antibodies, ligands, receptors, etc. exist in blood. Therefore, various methods and apparatuses for detecting analytes related to troubles and disease from whole blood has been developed. Meanwhile, blood corpuscles in an extremely small amount, transitional epithelial cell (diameter: 20~40 μm), and squamous epithelial cell (diameter: 40~60 μm) are included in urine.

Research for rapidly obtaining various pieces of information from end blood collected in a clinic by using a lab-on-μ chip in analysis of blood has been recently progressed. As a result, a rapid-chip or a rapid-kit has been developed. As shown in FIG. 1, a kit disclosed in U.S. Pat. No. 6,485,982 applied by Armkel, LLC Corp includes a filtering process, in which a blood sample is diluted and a porous membrane is used, as a essential process. In a reaction zone, conjugation between an analyte and a marker so as to allow the analytee to be labeled by the marker, e.g. fluorescent material, bonding between the marker and a probe, and cleaning are performed in the membrane. This kit provides a relatively high effective volume ratio due to low hematocrit since this kit uses a diluted blood sample. However, there is a problem in that the kit is not suitable for quantitative analysis, and pre-processes, such as dilution, etc. make it difficult to rapidly detect analytes (see Table 1).

TABLE 1

| Characteristic | Volume (μl) Qualitative/Semi-quantitative analysis |
| --- | --- |
| 1. Sampling | >100 |
| 2. Filtering | 18 |
| 3. Labeling (conjugation) | 8 |
| 4. Binding reaction | 10.2 |
| 5. Cleaning | 23.8 |
| Effective volume ratio (3 + 4 + 5)/(1) | <42% |

Filtering (2) is performed in a preprocessing unit in a chip, and labeling (3), binding reaction (4), and cleansing (5) are performed in the reaction zone.

Meanwhile, U.S. Pat. No. 6,905,882 applied by Biosite corp. discloses a chip, which has a structure where flux of fluids can be controlled through a micochannel and material of a substrate (hydrophile property/hydrophobic property), and can be coupled with a known porous membrane so as to be used. That is, it is suggested that the movement speed of fluids in a sample injecting part and the reaction zone can be controlled by selectively using a microchannel or material of a substrate (hydrophile property/hydrophobic property). Also, a chip invented by Biosite corp. has a reaction zone implemented in a fluidic channel instead of a membrane. Therefore, all of conjugation between makers and analytes, reaction between analytes and probes, and cleansing are performed within the microchannel (see table 2). In a case where this chip is used in blood analysis, quantitative analysis is possible, and whole blood can be used without pre-processes, such as diluting, etc. However, due to high hematocrit of a sample, there is a very low effective volume ratio, which means an amount of a sample taking part in reaction, which is required for detecting an initial injected amount of a sample (see table 2). Also, in a case where filtering isn't performed, a large amount of noise materials in addition to analytes moves through a channel so that it is very difficult to obtain an accurate analysis result. Therefore, in order to perform accurate analysis, an additional filtering means or step is necessarily required.

TABLE 2

| Characteristic | Volume (μl) quantitative analysis |
|---|---|
| 1. Sampling | 140~150 |
| 2. Filtering | 105 |
| 3. Labeling (conjugation) | 1 |
| 4. Binding reaction | 5 |
| 5. Cleaning | 25 |
| Effective volume ratio (3 + 4 + 5)/(1) | 12~22% |

Filtering (2) is performed in a preprocessing unit in a chip, and labeling (3), binding reaction (4), and cleansing (5) are performed in the reaction zone.

Other blood analysis chips (a rapid-chip) substantially include a filtering process as an essential process. Filtering, and particularly filtering using a paper filter, causes dead volume of a sample fluid because the sample fluid is absorbed in the filter. Consequently, in order to detect and analyze analytes existing in the sample, a minimum injection amount of a sample (in a case of hematologic analysis, >100 μl) is required. This makes it impossible to detect and analyze analytes existing in fluids in the minimum amount. Thus, research about micro fluidics has been continuously progressed so as to replace a paper filter. However, in reality, dead volume of a sample fluid hasn't been decreased until now.

Thus, the present inventors have developed a module where a filtering zone and a reaction zone for detecting and analyzing analytes in fluids are implemented in a microchannel, and have manufactured a chip having the module. Also, detecting analytes from the minimum amount of sample fluid has been performed. As a result, dead volume of the sample fluid was remarkably reduced so that it was confirmed that quantitative and qualitative analysis can be rapidly performed by using the minimum amount of the sample. Accordingly, based on the above conformed fact, the present invention was invented.

DISCLOSURE

Technical Problem

The present invention has been made in view of the above-mentioned problems, and the present invention provides a module for detecting analytes in fluids, which includes a filtering zone for removing noise materials, a reaction zone where reaction for detecting analytes is performed, and also includes a microchannel through which a sample fluid moves.

Also the present invention provides a chip having the module.

Technical Solution

In accordance with an aspect of the present invention, there is provided a module for detecting analytes in fluids, the module having a microchannel, noise materials being removed due to the height of the microchannel, a reaction zone where a reaction for detecting analytes is performed being included in the closed microchannel, and a filtering zone and the reaction zone being integrally formed in the microchannel.

In accordance with another aspect of the present invention provides a module for detecting analytes in fluids, the module including: a sample injecting part for injecting sample fluid; a filtering zone for removing noise materials; and a reaction zone where reaction for detecting the analytes is performed, wherein the filtering zone and the reaction zone are included in a microchannel. The height of the microchannel is h or more and less than H, the width of the microchannel is 2H or more and less than L, height h is a minimum height allowing analytes existing in the fluid to pass through the microchannel, height H is a minimum height allowing noise material existing in the fluid to pass through the microchannel, and L is a width of a substrate. The width of the microchannel preferably is 2H, which allows analytes except for noise material to moves through the microchannel.

In accordance with another aspect of the present invention provides a chip for detecting analytes in fluids, the chip including at least one sample inlet extending outside of the chip and at least one sample outlet extending outside of the chip, wherein the sample inlet and the sample outlet communicate with at least one module, Moreover, the present invention provides a chip for detecting analytes in fluids, which has a structure where a sample inlet and a sample outlet, which extends outside of the chip, are included, and at least one sample inlet and at least one sample discharging opening communicate with each other through at least one module. As such, in a fluid analysis chip according to the present invention, while sample fluid flows into a microchannel, noise materials are substantially filtered due to capillary force and a limited height of the microchannel so that value of [noise materials]/[analytes] of the sample fluid can be reduced to a level very near 0 at the reaction zone. Moreover, there is no reduction of effective volume ratio according to dead volume of a sample due to use of a conventional separate filtering means, e.g. a paper filter.

In a chip for detecting analytes in fluids according to the present invention, the sample inlet is included at an upper substrate, or a channel extends from a side surface of the substrate so as to communicate with the outside (see FIG. 6). The below table 3 and table 4 shows comparison between a case where blood is analyzed by using a chip according to the present invention and a case where blood is analyzed by using a conventional chip.

TABLE 3

|  | Only porous membrane is used | Membrane + microchannel | Only microchannel is used |
|---|---|---|---|
| Separation of blood plasma | Porous membrane | Porous membrane | — |
| Reaction | Microchannel | Microchannel | Microchannel |
| Cleaning | Microchannel | Microchannel | Microchannel |
| Patent | US patent registration No. 6485982 | US patent registration No. 6905882 | The present invention |

TABLE 4

|  | Only porous membrane is used | Membrane + microchannel | Only microchannel is used |
| --- | --- | --- | --- |
| Analysis type | Qualitative analysis | Quantitative analysis | Quantitative analysis |
| The amount of sample [µl] | 5(blood) + 95 (diluted liquid) → total 100 | 140~250 | <5 |
| Reaction period of time | After and before 15 minutes | After and before 15 minutes | Within five minutes |
| Convenience | Pre-processing of sample (blood is diluted by using diluted liquid) | No pre-process | No pre-process |

As such, in the module and the chip having the module according to the present invention, it is possible to rapidly detect and analyze a minimum amount of analytes included in the sample from the minimum amount of the sample fluid.

According to one embodiment, the module and the chip having the module according to the present invention includes a reservoir disposed at a sample injecting part, the reservoir having an expanded recess-shape having a sectional area larger than a sectional area of a microchannel near to a lower part of the sample inlet. Therefore, the microchannel communicates with the sample inlet after passing by the reservoir, and the reservoir has a height higher than the microchannel (see FIGS. 4 and 7). The height of the reservoir is higher than the height of the microchannel so that a coefficient of viscosity of fluids moving due to Fahreus-Lindquist effect (reference: Biomechanics: Motion, Flow, Stress and Growth) is remarkably reduced while moving from the reservoir to the microchannel. Therefore, in a case where the module and the chip according to the present invention are used in blood analysis, hematocrit within the microchannel is reduced.

The fluid analysis chip according to the present invention may include at least one sample inlet, at least one reservoir, at least one module according to the present invention, and at least one sample outlet (see FIG. 8).

As described above, in the chip according to the present invention, analytes in fluids moving through a microchannel are bound to material, e.g. protein, antigens, antibodies, DNA, RNA, or a receptor, which are immobilized on the bottom surface of the channel and specifically react with the analytes, and are detected and analyzed by a detecting means. According to necessity, it is possible that analytes are labeled before the analytes are coupled to material fixedly bonded to a substrate. For example, in a case where antigen A in a sample fluid is detected, after performing conjugation between antigen A and fluorescent material, antigen A is used in detection in such a manner that the conjugation between antigen A and the fluorescent material is fixed by using antibodies respective to antigen A, which is bound to the substrate. The below [table 5] shows signal detecting systems including various signal generating conditions and signal detecting methods, which can be used in detecting analytes in a reaction zone within the module of the chip according to the present invention.

TABLE 5

| Measurement means | Signal generation condition | Measurement method |
| --- | --- | --- |
| Optical means | Optical stimulation/reaction | Fluorescence, Interrometry, ellipsometry |
|  | Electrical and chemical stimulation/reaction | ECL(Electro generated Chemiilluminescence) |
|  | Bio-chemical stimulation/reaction | ElISA (enzyme linked immunosorbent assay) |
| Electric means | Voltage apply | Electrical Detection (resistance change detection)FET (Field Effect Transistor) Impedance Resistance Capacitance |
|  | Bio-chemical stimulation/reaction | Enzyme-linked Electro Chemical Detection |
| Physical means | Leading vibration of a predetermined frequency | QCM (Quarts Crystal Microbalance) SAW (Surface Crystal Microbalance) Cantilever |

As such, the chip according to the present invention can be widely used in various fields including detecting various chemical compounds, detecting material noxious to the environment by using the detected chemical compounds, blood analysis, urine examination, an immunity test through antigen-antibody reaction, searching for candidate material to be new drug through ligand-receptor binding, DNA/RNA analysis, etc. Moreover, at least two modules can be included so that at least two analytes can be detected and analyzed simultaneously.

FIG. 12 shows a method for comparing an analyte a1 in one channel with a control group b1, and FIG. 13 shows a method for comparing three analytes a1, a2, and a3 with three control groups b1, b2, and b3 and detecting them. Also, FIG. 14 shows a method for comparing three analytes a1, a2, and a3 with one control groups b1.

According to one embodiment, at least two microchannels are branched from other microchannel connected with a reservoir so that they indirectly communicate with the reservoir. The microchannel connected with the reservoir includes a micro-valve and is provided with a chip having a structure which can control the flow of fluid (see FIG. 9).

According to one embodiment, the module and the chip according to the present invention are used in blood analysis. In a case where the chip according to the present invention is used in blood analysis, it is possible to detect analytes within five minutes by using whole blood in am amount less than 5 µl. As shown in FIG. 3, the blood analysis chip according to the present invention can use whole blood in an amount of less than 5 µl without a need for performing a pre-process. If blood is injected into the blood analysis chip according to the present invention as shown in FIG. 4, a blood sample moves toward a sample outlet due to capillary force. Also, noise materials within the blood, e.g. blood corpuscles, can not move through the channel due to the limited height of the channel (1~10 µm), and remain at a sample injecting part or a reservoir. Therefore, all processes of filtering, labeling analytes, binding between the analytes and probes, and cleansing are performed in the microchannel. At this time, an effective volume ratio indicated as [the amount of the injected sample−the loss amount of the sample]/[the amount of the injected sample] is 50~100%, which shows a very remarkable result in comparison with a conventional technique.

Advantageous Effects

As such, a module and a chip according to the present invention can remove and detect noise materials by a microchannel. Therefore, an effective volume rate of 50~100% is implemented so that analytes existing in a fluid can be effectively detected from the fluid in a minimum amount. The present invention can be used in analyzing various kinds of fluids.

BRIEF DESCRIPTION OF THE DRAWINGS

The foregoing and other objects, features and advantages of the present invention will become more apparent from the following detailed description when taken in conjunction with the accompanying drawings in which.

MODE FOR INVENTION

Hereinafter, exemplary embodiments of the present invention will be described with reference to the accompanying drawings.

As a term used in the present invention, "a closed channel" means a channel, which is formed at an interior of a chip and has a structure shaped like a pipe, in which fluids aren't exposed outside of the chip while moving through the channel.

As a term used in the present invention, "a channel inner wall" means each surface of a channel limiting space, through which fluids flow, at the interior of a chip.

As a term used in the present invention, "effective volume rate" means [an injected amount of fluidic sample−an amount of dead volume of sample fluid]/[an injected amount of sample fluid].

As a term used in the present invention, "pre-processing unit" is a unit performing a process of diluting a sample fluid, etc. so as to detect and analyze analytes in the sample fluid.

As a term used in the present invention, "a filtering zone" of the sample fluid means a zone for removing noise materials so as to detect and analyze analytes in the sample fluid.

As a term used in the present invention, "a reaction zone" is a zone within a microchannel where analytes and signal generating materials react against each other, and the analytes are mobilized on a substrate.

Hereinafter, a fluid analysis chip manufactured according to one embodiment will be described in detail with reference to accompanying drawings.

Embodiment 1

Manufacturing a Fluid Analysis Chip

Figure 1:
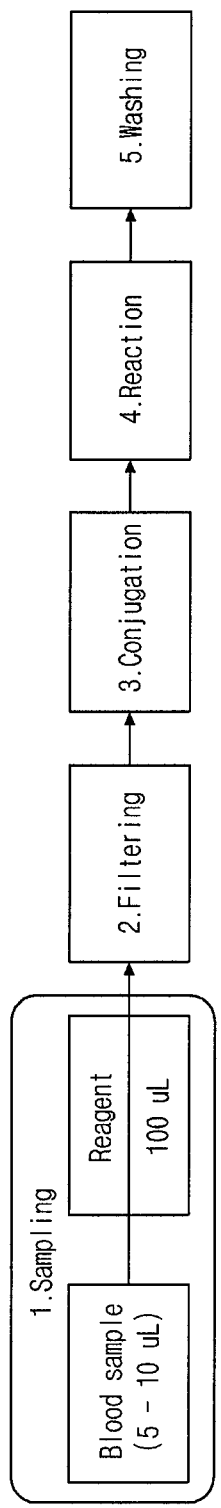
FIG. 1 is a view showing a process of detecting analytes within a fluid by using a chip using a conventional membrane.
Figure 2:
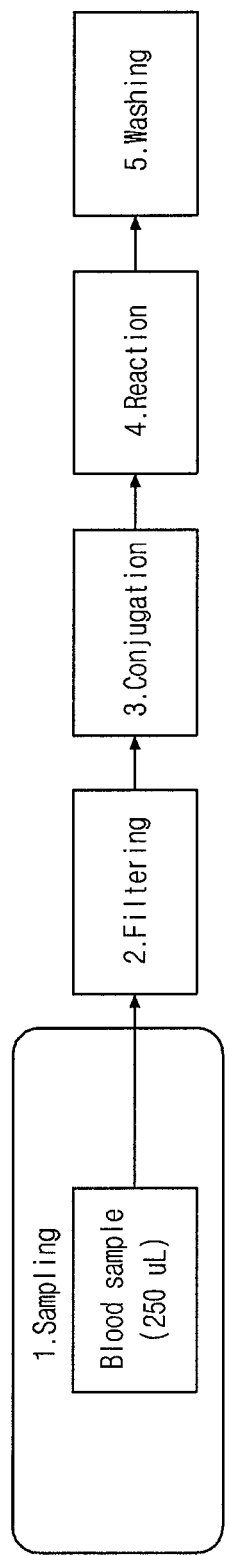
FIG. 2 is a view showing a process of detecting analytes within a fluid by using a chip for controlling the flux of the fluid by using a conventional microchannel.
Figure 3:
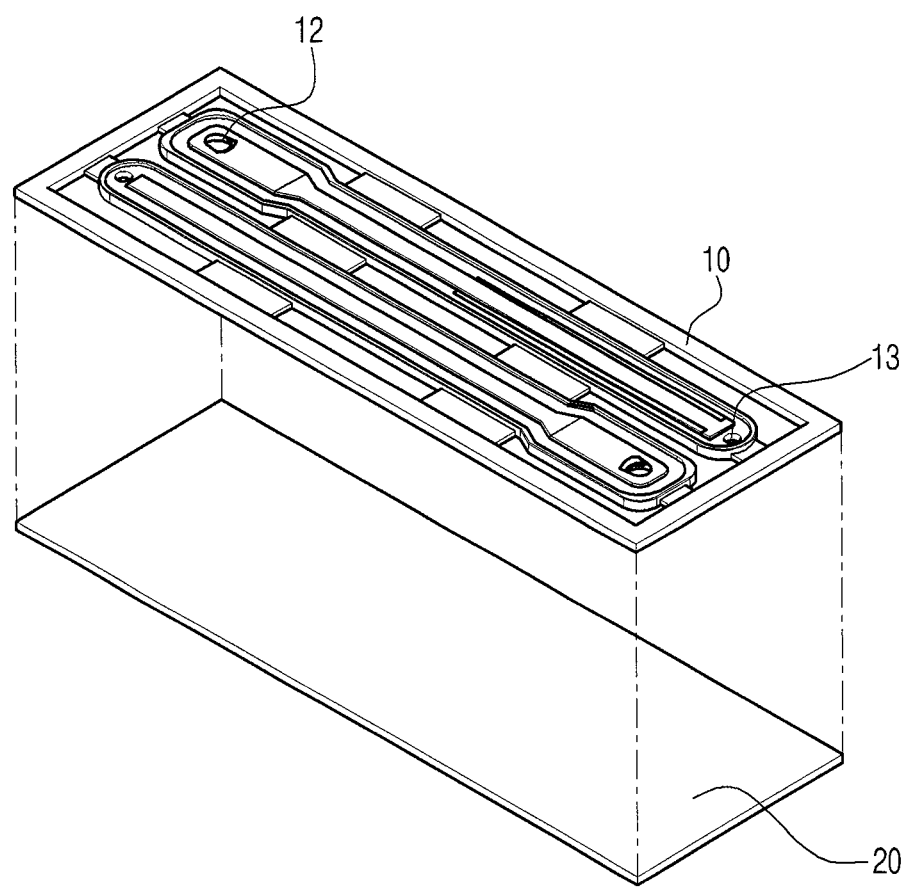
FIG. 3 is a perspective view of a fluid analysis chip according to a first preferred embodiment of the present invention.
Figure 4:
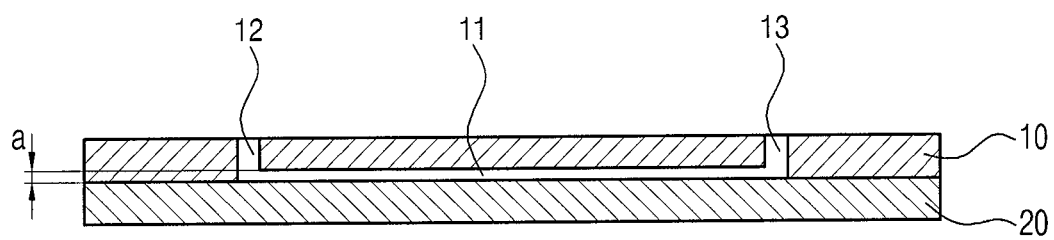
FIG. 4 is a sectional view of the fluid analysis chip shown in FIG. 3, in which the chip is cut off in a longitudinal direction.
Figure 5:
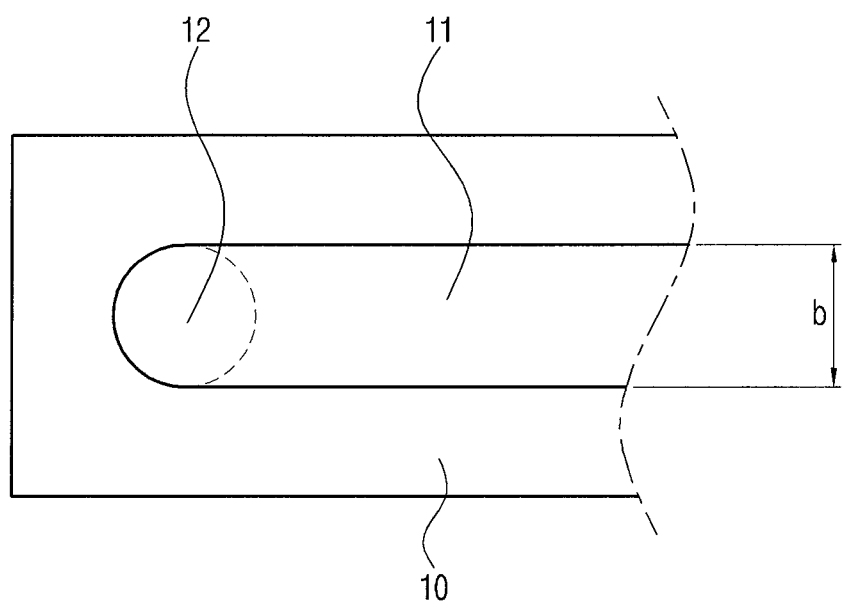
FIG. 5 is a sectional view of the fluid analysis chip shown in FIG. 3, in which the chip is cut off in a transverse direction.

FIG. 3 is a perspective view of a fluid analysis chip according to the first preferred embodiment of the present invention, FIG. 4 is a sectional view of the fluid analysis chip shown in FIG. 3, in which the chip is cut off in a longitudinal direction, and FIG. 5 is a sectional view of the fluid analysis chip shown in FIG. 3, in which the chip is cut off in a transverse direction.

As shown, the chip according to the first preferred embodiment of the present invention has a structure where an upper plate 10 and a lower plate 20 are assembled with each other. A module included in the chip includes a microchannel 11, which is recessed on the upper plate 10 with a predetermined depth and extends in a longitudinal direction so as to form an airtight space when the upper plate 10 is assembled with the lower plate 20. The microchannel has one end with a filtering zone, which is connected with a sample inlet 12 extending outside of the microchannel so as to allow the microchannel 11 to communicate with the outside, and the other end connected with a sample outlet 13.

As shown in FIG. 4, the height of the microchannel 11 is higher than height h of an analyte existing in an injected sample fluid, and is lower than height H of noise material existing in the injected sample fluid. As shown in FIG. 5, width b of the microchannel 11 is more than two times larger than height H of noise material existing in the injected sample fluid and is smaller than width L of a substrate.

In a case where the chip according to the first preferred embodiment of the present invention is used in blood analysis or urine analysis, it is preferable that height a of the microchannel 11 is 1~10 μm so as to interrupt the flow of blood-corpuscles, which are noise materials.

When whole blood as a sample fluid is injected into the chip, which is structured as described above according to the first preferred embodiment of the present invention, through the sample inlet 12, the fluidic sample moved toward the sample outlet 13 after passing by the microchannel 11 due to capillary force, and blood-corpuscles, which are noise materials in whole blood, can not move into the microchannel 11 due to height a of the microchannel 11, and remains where they are. Also, a reaction zone is implemented in the microchannel 11. While blood in a state where the number of blood-corpuscles is decreased moves within the microchannel 11, labeling analytes, binding between the anlaytes and probes, and cleaning are performed in the reaction zone.

Figure 6:
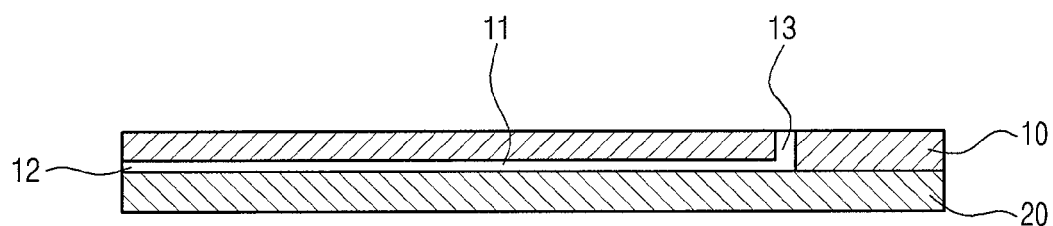
FIG. 6 is a sectional view of a fluid analysis chip according to a second preferred embodiment of the present invention, in which the chip is cut off in a longitudinal direction.

Similarly, as shown in FIG. 6, a fluid analysis chip according to a second preferred embodiment of the present invention has a microchannel, which has one end extending to the outside of the chip so as to allow the microchannel to be directly connected with the outside, and includes a sample inlet 12 formed at the one end of the microchannel 11. In addition, the remaining structure and its function of the chip are equal to the first preferred embodiment of the present invention. At this time, it is also possible that the other end of the microchannel extends to the outside of the chip so as to allow the microchannel to be directly connected with the outside, and a sample outlet 13 is formed at the other end of the microchannel 11.

Figure 7:
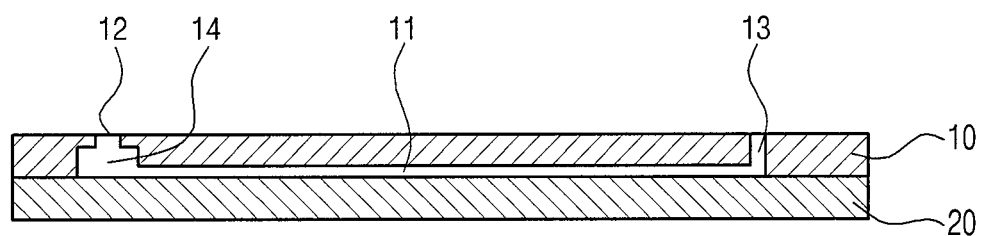
FIG. 7 is a sectional view of a fluid analysis chip according to a third preferred embodiment of the present invention, in which the chip is cut off in a longitudinal direction.

Similarly, as shown in FIG. 7, a fluid analysis chip according to a third preferred embodiment of the present invention has a reservoir 14 formed at a portion where a sample inlet 12 and the microchannel 11 are connected with each other. The reservoir 14 has a sectional area larger than a sectional area of the microchannel 11 so as to allow an injected sample fluid to temporarily remain in the reservoir. Also, the remaining structure and function of the chip is equal to the chip according to the first preferred embodiment of the present invention.

In the fluid analysis chip structure as described above according to the third preferred embodiment of the present invention, when a sample fluid is injected into the chip through the sample inlet 12, the fluidic sample temporarily remains in the reservoir 14. Therefore, due to potential energy of the sample fluid stacked in the reservoir 14, pressure is applied to the sample fluid introduced into the microchannel 11 so that the speed of the sample fluid flowing into the microchannel 11 increases.

Figure 8:
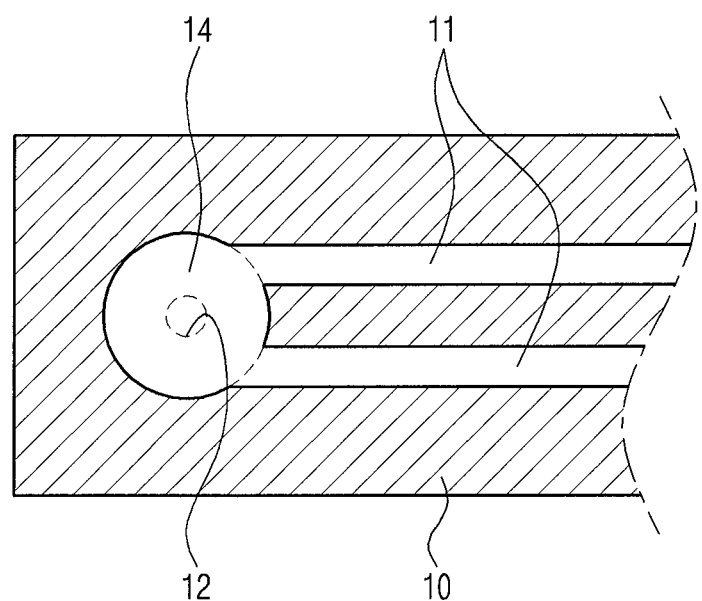
FIG. 8 is a sectional view of a fluid analysis chip according to a fourth preferred embodiment of the present invention, in which the chip is cut off in a transverse direction.

Similarly, as shown in FIG. 8, a fluid analysis chip according to a fourth preferred embodiment of the present invention has a structure where a plurality of microchannels 11 is branched from one reservoir 14, and they are preferably branched in one direction as shown. However, it is also possible that the microchannels are branched from one reservoir 14 in directions different from each other. Also, a structure where at least three microchannels are branched from the reservoir 14 is possible.

Also, the remaining structure and function are equal to them of the chip according to the third preferred embodiment of the present invention.

In the fluid analysis chip structure as described above according to the fourth preferred embodiment of the present invention, when a sample fluid is injected to the chip through the sample inlet 12, the fluidic sample temporarily remains in the reservoir 14. Therefore, due to potential energy of the sample fluid stacked in the reservoir 14, pressure is applied to the fluidic sample introduced into the plurality of microchannels 11 so that the speed of the sample fluid flowing into the microchannel 11 increases.

Figure 9:
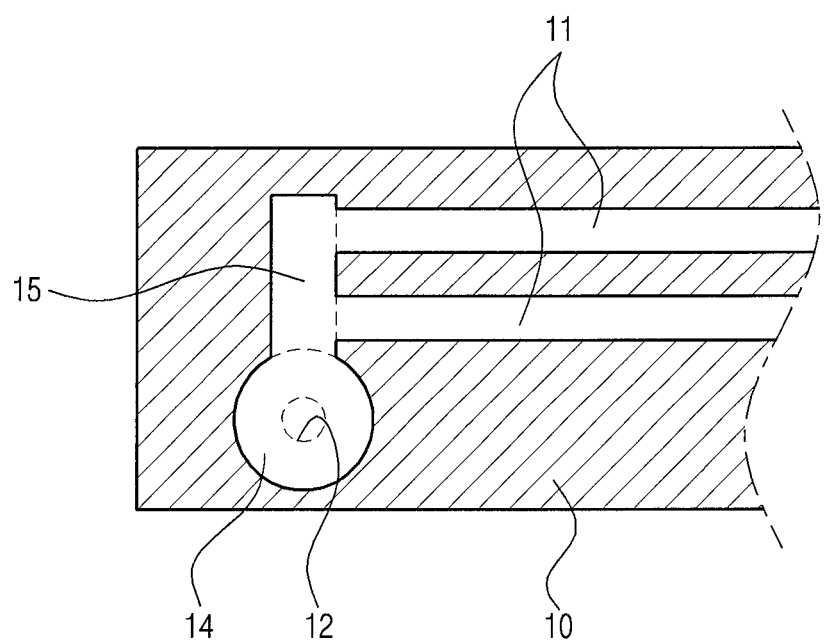
FIG. 9 is a sectional view of a fluid analysis chip according to a fifth preferred embodiment of the present invention, in which the chip is cut off in a transverse direction.

Similarly, as shown in FIG. 9, a fluid analysis chip according to a fifth preferred embodiment of the present invention has a structure where a middle channel 15 communicates with a reservoir 14, and a plurality of microchannels 11 is branched from the middle channel 15. The middle channel 15 is formed in such a manner that it is recessed on an upper plate 10 with a predetermined depth, so that an inner receiving space having a sectional area larger than a sectional area of each microchannel 11 is formed when the upper plate is assembled with a lower plate. Also, the remaining structure and function are equal to them of the chip according to the fourth preferred embodiment of the present invention.

In the fluid analysis chip structure as described above according to the fifth preferred embodiment of the present invention, when a sample fluid is injected to the chip through the sample inlet 12, potential energy of the sample fluid is generated while the sample fluid temporarily remains in a reservoir 14 so that the progressing speed of the sample fluid increases due to the potential energy. When the sample fluid is introduced to a middle channel 15 after passing by the reservoir 14, the sample fluid sequentially flows into respective microchannels 11 while passing by the middle channel 15. Also, the middle channel has a valve so that it is possible to properly change flux of the fluid.

Similarly, although not shown, a system having a fluid analysis chip according to a sixth preferred embodiment of the present invention is a module for detecting analytes in fluids, which includes a sample injecting part for injecting sample fluid, a filtering zone for removing noise materials, and a reaction zone where reacting for detecting analytes is performed. The filtering zone and the reaction zone are included in a closed microchannel, through which sample fluid flows due to capillary floating. The height of the microchannel of the module is h or more and less than H, and the width of the microchannel is 2H or more and less than L. Height h is the minimum height allowing analytes existing in a sample fluid to pass through the microchannel, and height H is the minimum height allowing noise materials existing in the sample fluid to pass through the microchannel. Also, L is the height of a substrate. This system is a system having effective volume ratio of sample fluid, which is 50% or more.

Embodiment 2

Detecting Troponin I from Whole Blood

Figure 10:
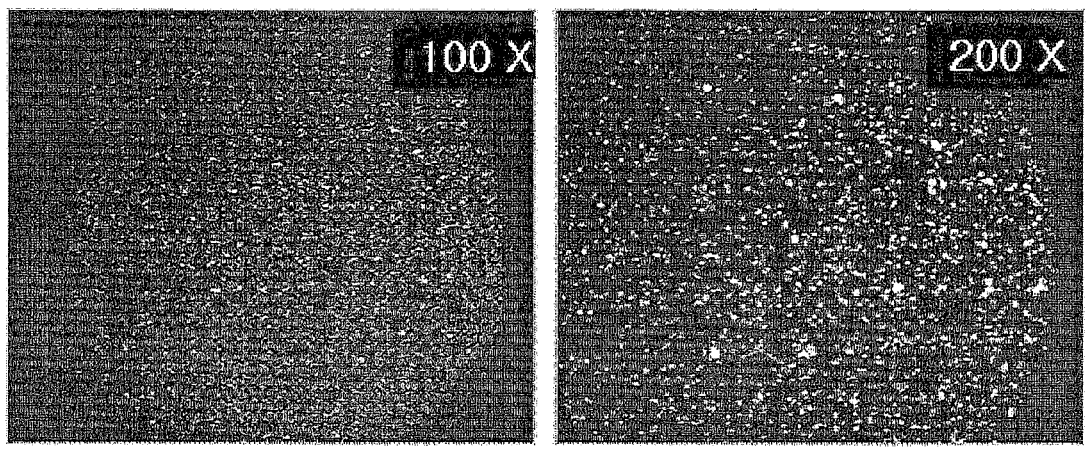
FIG. 10 is a fluorescent micrograph showing a result obtained by analyzing blood by using whole blood.
Figure 11:
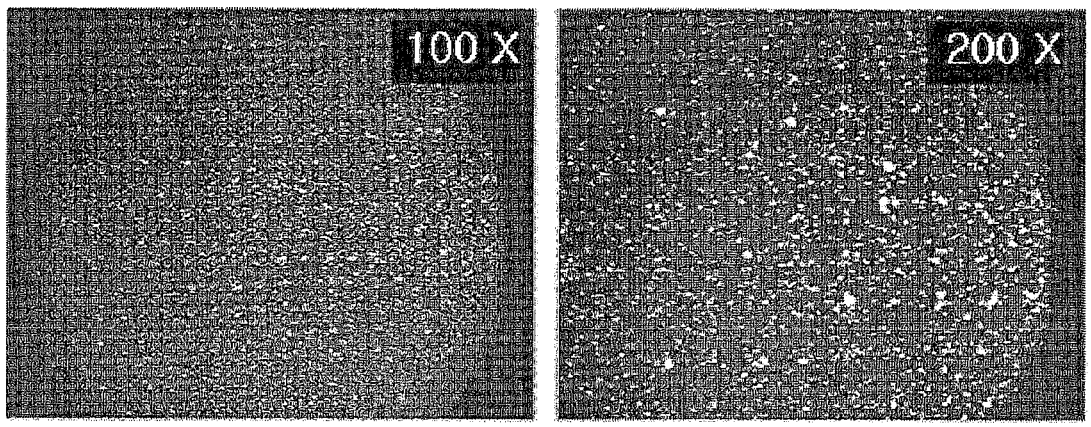
FIG. 11 is a fluorescent micrograph showing a result obtained by analyzing remaining blood after blood corpuscles are removed from whole blood.
Figure 12:
FIG. 12 is a schematic view showing a method for comparing one analyte in one channel with a control group.
Figure 13:
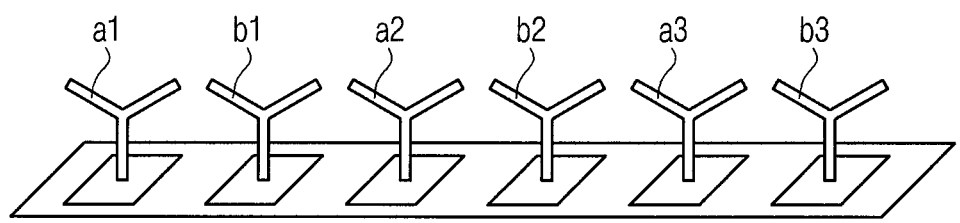
FIG. 13 is a schematic view showing a method for comparing three analytes to be analyzed with three control groups, respectively, and detecting the analytes.
Figure 14:
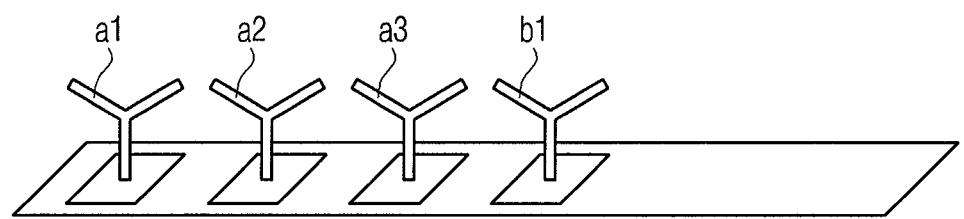
FIG. 14 a schematic view showing a method for comparing three analytes a1, a2, and a3 with one control group b1.

By using a chip, which has a structure equal to the structure of the microchannel 11 in embodiment 1 according to the present invention and has a microchannel with a height of 8 μm, Troponin I was detected from whole blood. Anti-Troponin I antibodies (clone 16A11, monoclonal, and Hytest), which are tagged with fluorescent material (Orange (540/560), Invitrogen) so as to label Troponin I, are temporarily immobilized on a substrate. Whole blood is injected into a sample inlet so as to remove blood corpuscles from the inlet of a micro channel, and Troponin I existing in the blood is bonded to the anti-Troponin I temporarily immobilized on the substrate. The whole blood was injected to the sample inlet-hole and the blood cell was removed of the entrance of microchannel. Subsequently, extra Troponin I tagged with fluorescent material, which didn't join in reaction, was removed by cleaning a chip. The level of fluorescent was checked by using a fluorescent microscope (see FIG. 10). As such, Troponin I was detected by using blood remaining after blood-corpuscles had been removed from the whole blood (see FIG. 12). As shown in FIGS. 10, 11, and 12, in a case where whole blood is used, the chip according to the present invention shows detection sensitivity, which is nearly equal to detection sensitivity in a case where blood without for blood-corpuscles is used.

Such an embodiment can be applied to detection of various analytes used in inspecting diseases shown in Table 6.

TABLE 6

| Disease | Detected material |
| --- | --- |
| Infectious Disease | Influenza, etc. |
| Ba-se-dow's | Thyroid Stimulating Hormone (TSH) |

TABLE 6-continued

| Disease | Detected material |
|---|---|
| disease | Triiodothyronine (T3) |
| | Thyroxine (T4) |
| | Triiodothyronine Free(FT3) |
| | Thyroxine Free (FT4), etc. |
| Osteoporosis | NTx, etc. |
| cardiac disorder | Troponin I |
| | CK-MB |
| | Myoglobin |
| | NT-proBNP |
| | D-dimer, etc. |
| Inflammatory disease | (hs-)CRP, etc. |
| Hormone | Growth hormone |
| | Luteinizing Hormone (LH) |
| | Cortisol |
| | Estradiol |
| | Progesterone |
| | hCG |
| | Testosterone |
| | Follicle Stimulating Hormone (FSH), etc. |

The invention claimed is:

1. A chip for detecting analytes in fluids, the chip comprising:
a sample inlet extending outside of the chip; and
a sample outlet extending outside of the chip, wherein the chip has a structure where the sample inlet and the sample outlet communicate with each other through a module, the module comprising:
a sample injecting part for injecting a sample fluid;
a filtering zone configured to remove noise materials from the sample fluid, the filtering zone having a height lower than that of the noise materials; and
a reaction zone arranged to perform a reaction to detect the analytes in the sample fluid,
wherein the filtering zone and the reaction zone are included in a closed microchannel, through which the sample fluid moves due to capillary floating,
wherein an expanding part, which has an expanded space having a sectional area larger than a sectional area of the microchannel, is formed at a part or whole part of each inner wall of both sides of the microchannel of the module.

2. The chip for detecting analytes in fluids as claimed in claim 1, wherein the sample inlet and the sample outlet communicate with each other through a plurality of modules.

3. The chip for detecting analytes in fluids as claimed in claim 1, further comprising a middle channel, which has an expanded inner space having a sectional area larger than a sectional area of the microchannel, formed between a plurality of microchannels comprising the microchannel and at least one additional microchannel.

4. The chip for detecting analytes in fluids as claimed in claim 2, further comprising a middle channel, which has an expanded inner space having a sectional area larger than a sectional area of the microchannel, formed between a plurality of microchannels comprising the microchannel and at least one additional channel.

5. The chip for detecting analytes in fluids as claimed in claim 1, wherein the sample injecting part has a reservoir, which has a height higher than a height of the microchannel and a sectional area larger than a sectional area of the microchannel, is included at a lower end of the sample inlet.

6. The chip for detecting analytes in fluids as claimed in claim 2, wherein each sample injecting part has a reservoir, which has a height higher than a height of the microchannel and a sectional area larger than a sectional area of the microchannel, is included at a lower end of the sample inlet.

7. The chip for detecting analytes in fluids as claimed in claim 3, wherein the sample injecting part has a reservoir, which has a height higher than a height of the microchannel and a sectional area larger than a sectional area of the microchannel, is included at a lower end of the sample inlet.

8. The chip for detecting analytes in fluids as claimed in claim 4, wherein each sample injecting part has a reservoir, which has a height higher than a height of the microchannels and a sectional area larger than the sectional area of the microchannel, is included at a lower end of the sample inlet.

9. The chip for detecting analytes in fluids as claimed in claim 1, wherein the sample fluid is a blood sample.

10. The chip for detecting analytes in fluids as claimed in claim 9, wherein a height of the microchannel of the module is 1~30 μm, and less than 100 μl of whole blood is used.

11. The chip for detecting analytes in fluids as claimed in claim 1, wherein a height of the microchannel is h or more and less than H, the width of the microchannel is 2H or more and less than L, height h is a minimum height allowing analytes existing in the sample fluid to pass through the microchannel, height H is a minimum height allowing noise material existing in the fluid to pass through the microchannel, and L is a width of a substrate.

* * * * *